United States Patent
Cronin et al.

(10) Patent No.: US 9,518,925 B2
(45) Date of Patent: Dec. 13, 2016

(54) HIGH RESOLUTION, WIDE DYNAMIC RANGE MICROFLUIDIC DETECTION SYSTEM

(71) Applicant: RADISENS DIAGNOSTICS LTD., Cork (IE)

(72) Inventors: Donal Cronin, Co. Cork Mallow (IE); Jerry O'Brien, Cork (IE); Lee Barry, Innishannon (IE)

(73) Assignee: Radisens Diagnostics Limited, Cork (IE)

( * ) Notice: Subject to any disclaimer, the term of this patent is extended or adjusted under 35 U.S.C. 154(b) by 54 days.

(21) Appl. No.: 14/367,353

(22) PCT Filed: Dec. 21, 2012

(86) PCT No.: PCT/EP2012/076719
§ 371 (c)(1),
(2) Date: Jun. 20, 2014

(87) PCT Pub. No.: WO2013/093035
PCT Pub. Date: Jun. 27, 2013

(65) Prior Publication Data
US 2014/0374622 A1  Dec. 25, 2014

Related U.S. Application Data

(60) Provisional application No. 61/579,506, filed on Dec. 22, 2011.

(30) Foreign Application Priority Data

Dec. 22, 2011  (EP) ..................................... 11195145

(51) Int. Cl.
*G01N 21/64* (2006.01)
*G01J 1/04* (2006.01)
(Continued)

(52) U.S. Cl.
CPC ......... *G01N 21/6486* (2013.01); *G01J 1/0418* (2013.01); *G01J 1/0492* (2013.01);
(Continued)

(58) Field of Classification Search
CPC .......... G01J 1/0418; G01J 1/0492; G01J 1/18; G01J 2003/1213; G01J 3/36; G01N 15/14; G01N 15/1484; G01N 2021/6421; G01N 2021/6471; G01N 21/645; G01N 21/6486; G01N 21/76; G01N 2201/066; G01N 2201/12

See application file for complete search history.

(56) References Cited

U.S. PATENT DOCUMENTS 5,491,548 A   2/1996   Bell et al.
6,355,921 B1  3/2002   Staton et al.
(Continued)

FOREIGN PATENT DOCUMENTS

EP   1928167         11/2007
EP   2293032          9/2009
WO   2011026942 A2    3/2011

*Primary Examiner* — Francis M Legasse, Jr.
(74) *Attorney, Agent, or Firm* — K&L Gates LLP (57) ABSTRACT

The invention provides a high resolution, wide dynamic range, multi-color detection platform for microfluidic analyzers/instruments and methods. The detection platform uses multiple high gain semiconductor optical sensors for the detection of luminescence from cellular or biological samples. The digitized outputs from these sensors are combined and weighted in a signal processing unit, using predetermined algorithms for each color, which optimize the resolution in each of these high gain semiconductor optical sensors while extending the dynamic range of the detection platform.

11 Claims, 8 Drawing Sheets

(51) Int. Cl.
*G01J 1/18* (2006.01)
*G01J 3/36* (2006.01)
*G01N 21/76* (2006.01)
*G01J 3/12* (2006.01)
*G01N 15/14* (2006.01)

(52) U.S. Cl.
CPC . *G01J 1/18* (2013.01); *G01J 3/36* (2013.01); *G01N 15/14* (2013.01); *G01N 21/645* (2013.01); *G01N 21/76* (2013.01); *G01J 2003/1213* (2013.01); *G01N 15/1484* (2013.01); *G01N 2021/6421* (2013.01); *G01N 2021/6471* (2013.01); *G01N 2201/066* (2013.01); *G01N 2201/12* (2013.01)

(56) References Cited

U.S. PATENT DOCUMENTS

| | | | |
|---|---|---|---|
| 7,683,299 B2 * | 3/2010 | Patt | G01J 1/4228 250/201.1 |
| 2003/0058433 A1 | 3/2003 | Almogy et al. | |
| 2005/0151964 A1 | 7/2005 | Roth | |

* cited by examiner

HIGH RESOLUTION, WIDE DYNAMIC RANGE MICROFLUIDIC DETECTION SYSTEM

CROSS REFERENCE TO RELATED APPLICATIONS

This is the national phase under 35 U.S.C. §371 of International Application No. PCT/EP2012/076719 filed on Dec. 21, 2012, which claims priority to and benefit of European Application No. 11195145.5 filed on Dec. 22, 2011, and U.S. Provisional Application No. 61/579,506 filed on Dec. 22, 2011, the entire disclosures of each of which are incorporated by reference herein.

FIELD OF THE INVENTION

This invention relates generally to a microfluidic platform comprising a high resolution detection system and method for the detection of luminescence from cellular or biological samples over a wide dynamic range.

BACKGROUND TO THE INVENTION

Light emitted and scattered from samples is widely used to determine their cellular or biological content. It is desirable to have a multi-colour detection system that allows analysis of a wide optical detection range of biological samples, with high resolution, instantaneously for a variety of assays in immunology, biochemistry, and haematology for example. Pre-defined algorithms combining multi-sensor outputs in a multi-colour detection platform would provide the end-user with the capability of running these assays without the need for detailed knowledge of the technology and with minimal interaction and analysing it with high resolution over an extended dynamic range.

Photodetectors are required to detect and quantify this light from a sample under test, when stimulated by some form of luminescence. Photodiodes, arrays of photodiodes, CCDs and other solid state sensors can be used to quantify this light; however Photomultiplier Tubes (PMT's) are the incumbent photodetector of choice to detect such light components. This is due to their low-end sensitivity and ability to resolve over the PMT's dynamic range due to their internal gain structure (>10 e6).

However, a number of problems exist in that PMT's are expensive, require very high voltage operation, are not suited to point of care diagnostic instruments and settings due to their size, require complex and expensive optical arrangements, with PMT based instruments requiring specialised and expensive maintenance. A PMT's practical optical dynamic range is typically 3 decades, so to adjust its optical range of sensitivity to quantify the light emitted or scattered from a sample requires the bias voltage to be adjusted by a skilled operator trained in the use of each specific instrument.

Due to recent advances in high gain semiconductor optical sensors such as avalanche photodiodes (APDs), Geiger-mode avalanche photodiodes and arrays of these Geiger-mode detectors (referred to as Silicon Photomultipliers or SiPMs for short) they are beginning to replace PMT's in such analysers. For example EP2293032A1, assigned to the applicant of the present invention and incorporated herein by reference, describes an integrated cytometric sensor system using SiPMs and other advances to solve such aforementioned issues. The main advantages relate to lower cost and size, lower voltage operation, faster start-up times, scope for increased semiconductor integration and lower maintenance requirements. These advances open the possibility of bringing advanced central laboratory techniques, such as the gold standard method of clinical flow cytometry, into decentralised point-of-care environments for screening of patients' blood for various infectious diseases, chronic and acute conditions, viruses and blood ailments.

Similar to PMTs, solid state sensors that contain an internal gain structure, like APDs and SiPMs, allow their region of sensitivity to be selected for the sample under test, by altering their operating voltage. This is controlled somewhat by setting their voltage bias with respect to their breakdown voltage.

By setting the bias voltage higher than the breakdown voltage (placing the SiPM in Geiger mode) these high gain semiconductor optical sensors can detect dimmer light, but saturate easily in the presence of bright light. By lowering the bias voltage towards the breakdown voltage or below it (placing the SiPM in its linear mode of operation), brighter light can be detected before saturation occurs, but the solid state sensor will be less sensitive to dimmer light as a consequence.

Lowering the bias of a high gain semiconductor optical sensor extends its dynamic range, enabling the detection of brighter light at the expense of reducing resolution. This is due to the reduction in the sensor's internal gain with reducing bias voltage and hence reduction of the optical sensor's output photocurrent and responsivity. This compromise between resolution and dynamic range limits the ability of an optical system using two or more sensors biased at different bias levels to resolve between biological samples or cells with similar but distinct high light level intensities, thereby limiting the range and/or resolution of the system. EP 2293032A1 uses such a method of adjusting the bias voltage of the sensor for wide dynamic range operation in an integrated multi-colour cytometric sensor based on high gain semiconductor optical sensors such as SiPMs. A problem with this method is that the reduction in bias will minimize the resolution of the system.

Additional systems where a multi-sensor approach is used to extend the dynamic range of an optical detection system is disclosed in US 2005/0151964 which outlines the expansion of its dynamic range by splitting the fluorescent light over multiple paths with different intensities onto multiple sensors/channels. It is then determined which channel is operating in its linear range and the output signal adjusted according to the intensity of light, using post processing techniques.

U.S. Pat. No. 5,491,548 similarly produces a wide dynamic range output from two optical sensors where a percentage of light is split onto the first sensor and the remainder is transferred onto the second sensor and the outputs are combined digitally to produce a composite signal. However this invention uses two different types of sensor to detect the light. Additionally, the use of a switch ensures that only the data from one of these sensors can be used at a time.

U.S. Pat. No. 6,355,921B1 describes a method where the output signals from multiple PMTs are combined to increase the dynamic as in the other prior art. Also the dynamic range of each PMT individually can also be increased by using a control circuit to combine the output from a low light level detection circuit and a similar bright light level detection circuit where needed. EP 1928167A1 involves using multiple detectors again and adjusting their parameters using a signal processing unit in a targeted manner. One detector is adjusted to a dynamic range for a maximum level of electromagnetic radiation expected, while the other detector is adjusted to a reduced dynamic range for small and middle signal levels in order to obtain a higher signal to noise ratio (SNR) for these. These systems rely on a number of physically different detectors with different surface area and active areas and cannot work using a single type of detector. Additionally the sensors are mounted as a single array and does not use a beam splitter.

It is an object of the invention to provide a system and method to overcome at least one of the above mentioned problems.

SUMMARY OF THE INVENTION

According to the invention there is provided, as set out in the appended claims, a microfluidic platform comprising a multi-colour detection system which uses a combination of multiple high gain semiconductor optical sensors such as SiPMs using pre-determined algorithms to maintain high resolution while extending its dynamic range and methods are provided. These methods expand the system's dynamic range beyond what can be achieved with any single photodetector, while ensuring a low cost, miniaturised instrument for instantaneous high resolution detection of a wide range of optical intensities from cellular or biological samples.

In summary, the present invention provides a high resolution, wide dynamic range, multi-colour and sensor detection system designed specifically for high gain semiconductor optical sensors such as SiPMs. This is due to the non-linear internal gain profile of SiPMs compared to the linear profile of competing high gain photodetectors such as PMTs, such that a pre-defined algorithm per colour is required to select the high gain region of these sensors. The high gain region is used to maintain the resolution in this semiconductor based system and present a wide dynamic range by combining and weighting the outputs from the multiple sensors per colour.

This multi-colour detection system can be predominantly used for luminescence detection in microfluidics systems such as flow cytometers and centrifugal microfluidic platforms but not limited to these.

The invention provides a high resolution multi-colour detection system while providing wide dynamic range for each colour by combining the outputs of multiple high gain semiconductor sensors using pre-defined algorithms in a signal processing unit. This negates the need for sensor bias adjustment by the end user as done in the prior art, simplifying instrument usage particularly for POCT and clinical research.

In one embodiment there is provided multi-colour luminescence detection system in a microfluidic system, said detection system comprising:
   means for splitting light into at least two light paths for each detected colour of luminescence from a cellular or biological sample in the microfluidic system;
   a first high gain semiconductor optical sensor, for each luminescence colour component, adapted to be biased at an optimal operating voltage or gain for detecting low light levels of luminescence emitted from the cellular or biological sample with high resolution;
   a second high gain semiconductor optical sensor for each colour component adapted to detect higher light levels of luminescence, such that the light level falling on the second sensor is attenuated while maintaining resolution with a high gain setting; and
   means for processing per luminescence colour by combining and weighting the outputs from the first and second high gain semiconductor optical sensors using a signal processing unit, and providing an instantaneous multi-colour high resolution detection system over an extended dynamic range.

The optical dynamic range of the detection system for any specific wavelength of interest can be increased by using multiple high gain semiconductor optical sensors, collecting the emitted or scattered light from the luminescence sample at one or multiple points and directing the light to these sensors. Simultaneous measurements from two or more of these sensors per colour are collected, from the same sample of interest, and coupled together by a pre-defined algorithm in a signal processing unit to construct a wide dynamic range output for each colour. The algorithm for each colour is defined at an initial calibration stage where the algorithm coefficients that combine and weight the sensor combinations are determined by a monochromatic linear light source. The algorithms are then applied to the signal processing unit for each colour.

To pass the data from the multiple sensors to the signal processing unit, the photocurrent passed from the high gain semiconductor optical sensors due to luminescence stimulus are first amplified and converted into a voltage using a trans-impedance amplifier or similar arrangement. The outputs are digitized using an analogue to digital converter and then passed to the signal processing unit to process these individual outputs to create a composite output per colour. While extending the dynamic range is possible by splitting the light to multiple high gain semiconductor optical sensors, the gain setting for each of these will be optimised to maintain high resolution over the complete dynamic range as part of the pre-calibration sequence in defining the algorithms for each colour.

The primary sensor(s) of the system are optimised to detect low optical intensities to maximise the sensitivity of the system by selecting an appropriate gain setting that also maintains high resolution. Further sensor(s) are then used, with similar high gain settings, to detect brighter luminescence levels and the light falling on these sensor(s) is attenuated to maintain the resolution of the sensor's optimal gain setting without saturating the sensor's output.

This is specifically important for high gain semiconductor optical sensors like SiPMs as they have an optimal gain region, which also provides high resolution, as determined by their bias voltage. The outputs from these sensors which is digitized and then combined by a pre-defined algorithm, provides instantaneous, high resolution, multi-colour luminescence detection over a wide optical range of interest. This high resolution, wide dynamic range detection system would be pre-configured in a microfluidic based instrument and alleviates the need for end-user intervention in setting the optimal gain of the sensor(s) for each sample under test. This will allow the quantification of biological samples over many decades of dynamic range without any user intervention as required in current instruments/analysers In one embodiment the collected luminescence is split into specific wavelengths of interest by using coated beamsplitters or dichroic mirrors and additional optical filters where required. These mirrors and filters are grouped with the high gain semiconductor optical sensors and additional optical components, where required, to create a filter cell.

In one embodiment the light collected from the sample is directed to a single light path using light collection optics and focused onto 2 or more high gain semiconductor optical sensors. The photocurrent output is converted to the digital domain from these sensors and merged together using the pre-determined algorithm in the signal processing unit to produce a composite output.

Other embodiments show the light collected from the sample from multiple locations or collection points and merged to produce a high resolution, wide dynamic range detection system also.

A key criterion in each embodiment is to maximize the amount of light collected by sensor(s) of the detection system, particularly for low-light level detection systems where the light budget is limited.

In one embodiment the first and second optical sensors generate signals and adapted to be fed into a signal processing means to generate a wide dynamic range high resolution signal for each colour.

In one embodiment the sensors in the detection system are SiPMs.

In one embodiment more than one collection point is used to gather the light emitted from the luminescence sample to generate a high resolution, wide dynamic range output per colour.

In one embodiment, light emitted from the sample is coupled to a collector and passed through at least one filter adapted to attenuate the light level and delivered to said second high gain semiconductor optical sensor for each colour.

In one embodiment a collector is adapted to collect light from the sample and directed to a beam splitter.

In one embodiment the collector comprises a lens system.

In one embodiment the beam splitter is adapted with two or more output ports for delivering light to said first and second high gain semiconductor optical sensors for each colour.

In one embodiment the beam splitter comprises an uncoated mirror, said uncoated mirror adapted to deliver maximum amount of light via a first port to the first high gain semiconductor optical sensor detecting low-end light levels while bright light components of the sample are detected simultaneously at the second port by said second high gain semiconductor optical sensor.

In one embodiment the amount of light delivered from said first and second ports is dependent on the transmission or reflectance of the uncoated mirror.

In another embodiment of the present invention there is provided a system for detecting specific biological targets in a fluid sample or a non-fluidic sample adapted for luminescence detection at different wavelengths, said system comprising the detection system having:
  a first optical sensor biased at an optimal operating voltage or gain adapted for detecting low light levels of luminescence emitted from a cellular or biological sample; and
  a second optical sensor adapted to detect higher light levels of luminescence, such that the light level falling on the second sensor is attenuated; wherein processing of cellular or biological samples over many decades of dynamic range is achieved at high resolution.

In one embodiment, the light collected from the sample is coupled in free-space to two or more high gain semiconductor optical sensors for each colour on the same light path. 1 or more of these sensors contains an optical component such as a neutral density filter or similar in the light path to reduce the light level reaching the secondary sensor(s) here. By biasing the sensors in the attenuated section of this light path at a similar voltage bias to the primary sensor detecting low light levels, this ensures high resolution over the entire dynamic range of interest for each colour. The attenuation component(s) ensure the secondary sensor(s) do not saturate with this high resolution/gain setting.

In one embodiment, the light can be collected from multiple points and coupled to one or more sensors per colour with or without attenuating components attached.

Interleaving multiple sensor outputs for each colour from multiple collection points is carried out here to further enhance the dynamic range, while maintaining high resolution.

In one embodiment, the light collected from a single point is coupled to an array of high gain semiconductor optical sensors. The central sensor receives the maximum proportion of the collected light, particularly if the light beam has a Gaussian profile. This configuration serves to attenuate the light levels collected to the adjacent secondary sensors compared to the centre one which is used to collect the majority of the light from the sample. As the collected light to the secondary sensors is effectively attenuated using this method, a high bias/gain setting can still be applied to maintain resolution in the detection system, without saturating the outputs. The outputs from the arrays of sensors per colour are then coupled together in the processing unit to generate the high resolution, wide dynamic range output from the system. The arrangement of the sensors can be optimised to suit the light measurement and is not restricted to the embodiment shown here.

In one embodiment the secondary high gain semiconductor optical sensors may be different from the main sensor. They may be different in one or more aspects including, but not limited to pixel density, active area, sensor size, photon detection efficiency (PDE) or spectral responsivity.

In one embodiment the lens which couples the collected light to the high gain semiconductor optical sensor array may be adjustable, either manually or automatically. In one embodiment, some of the adjacent high gain semiconductor optical sensors of the sensor array per colour may contain attenuation filters also.

In one embodiment, the light can be collected from multiple points but just one high gain semiconductor optical sensor at each colour location, including attenuation filters if required.

In one embodiment, the light from the sample can be coupled from multiple points to multiple high gain semiconductor sensor arrays, with or without attenuation filters, to generate the high resolution, wide dynamic range output per colour.

In one embodiment, a beam splitter can be used to split the light collected from the sample simultaneously and couple it to the high gain semiconductor sensors for each colour. The split ratio of the beam splitter is used to attenuate the light to the secondary sensor(s) used to detect the higher optical power components from a sample. The processing unit again delivers a high dynamic range, high resolution output from these high gain semiconductor sensors for multiple wavelengths of interest.

In one embodiment the light is collected from multiple points and transferred to multiple beam splitters.

In one embodiment multiple sensors can detect the light from each port of the beam splitter and can also include a light attenuating component.

In a further embodiment there is provided a system comprising:
  a first optical sensor biased at an optimal operating voltage or gain adapted for detecting low light levels of luminescence emitted from a cellular or biological sample; and a second optical sensor adapted to detect higher light levels of luminescence, such that the light level falling on the second sensor is attenuated; wherein processing of cellular or biological samples over many decades of dynamic range is achieved at high resolution.

BRIEF DESCRIPTION OF THE DRAWINGS

The invention will be more clearly understood from the following description of an embodiment thereof, given by way of example only, with reference to the accompanying drawings, in which.

DETAILED DESCRIPTION OF THE DRAWINGS

Figure 1:
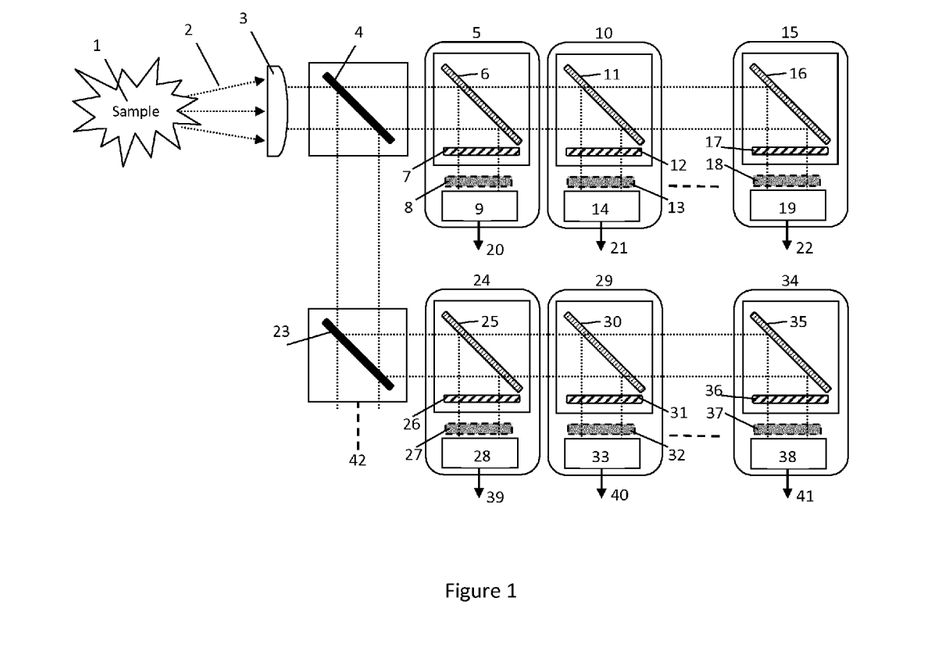
FIG. 1 illustrates a block diagram of the arrangement showing the multi-colour luminescence collected from a cellular or biological sample and distributed to wavelength specific filter cells that contain 1 or more high gain semiconductor optical sensors. The collected light is split between multiple light paths to extend the dynamic range for each luminescence colour of interest while keeping a high gain setting in all the sensors to maintain resolution.

FIG. 1 illustrates the fundamental block diagram of the multi-colour luminescence detection system presented in this invention. In this, the luminescence 2 is collected from a biological or cellular sample 1 in a microfluidic platform, that this detection system is housed in (not shown). The luminescence from the sample 1 is transferred to the detection system using a lens system 3. The collected luminescence 2 is then transferred to a beamsplitter or uncoated dichroic mirror 4 which diverts a percentage of this light along two light paths. The percentage of light sent along each light path depends on the transmission or the reflectance of the beamsplitter 4. The split ratio of the beamsplitter 4 can be such that the majority of light can be sent along either light path. It is assumed that the majority of the light is transmitted to the spectrally sensitive filter cells 5, 10 and 15. The remaining reflected light is sent to the corresponding filter cells 24, 29 and 34, via a reflective mirror 23. Each filter cell shown uses a combination of dichroic mirrors and bandpass filters, where required, to transfer wavelength specific light to 1 or more high gain semiconductor optical sensors. In any high gain semiconductor optical sensor system described in this invention, there can be between 1 and C colours of luminescence to discriminate between using the spectrally sensitive filter cells. For the first colour detected, the majority of light is detected using filter cell 5 which consists of a dichroic mirror 6 which reflects the wavelengths of interest and transmits the remaining spectrum to the adjacent filter cell 10. The reflected light from the dichroic mirror 6 in this filter cell 5, is transferred to 1 or more high gain semiconductor optical sensors 9 via a bandpass filter 7 and an attenuating component 8, in embodiments where required. An attenuating component is included in filter cells for detecting particular dynamic ranges of interest, while maintaining high resolution in the sensors. The remaining light from the beamsplitter 4 for the first colour of interest is detected by filter cell 24. Again, the light is reflected from the dichroic mirror 25 and transferred to 1 or more high gain semiconductor optical sensors 28 via a bandpass filter 26 and an attenuating component 27 in embodiments where required. The secondary sensor 28 for the first colour maintains a high gain setting but can detect bright luminescence samples without saturating, due to the reduction in light coming from the beamsplitter 4. The outputs 20 and 39 from the high gain semiconductor optical sensors 9 and 28 are then digitized and interleaved using a pre-determined algorithm, to create a high resolution, wide dynamic range signal dedicated to this spectral region of interest (see FIG. 2 description). The second of the C colours in the detection system is determined using the filter cells 10 and 29. The transmitted light from the dichroic mirrors 6 and 25 from the first colour strike the dichroic mirrors 11 and 30 respectively. The reflected light from the dichroic mirrors 11 and 30 for the spectral range of interest are transferred to the high gain semiconductor optical sensors 14 and 33 respectively. The outputs 21 and 40 from these are digitized and interleaved using a pre-determined algorithm, to create a high resolution, wide dynamic range signal dedicated to a second spectral region of interest. Bandpass filters 12 and 31 and attenuating components 13 and 32 are included in embodiments where required. The $C^{th}$ luminescence colour in the detection system is determined using the filter cells 15 and 34. The transmitted light from the dichroic mirrors from the previous filter cells strike the mirrors 16 and 35 respectively. The reflected light from the dichroic mirrors 16 and 35 for the spectral range of interest are transferred to the high gain semiconductor optical sensors 19 and 38 respectively. The outputs 22 and 41 from these are digitized and interleaved using a pre-determined algorithm, to create a high resolution, wide dynamic range signal dedicated to the $C^{th}$ spectral region of interest. Bandpass filters 17 and 37 and attenuating components 18 and 37 are included in embodiments where required. Additional beamsplitters with associated filter cells, 42, can be added to extend the dynamic range for each of the C colours of interest. In this case the reflective mirror 23 can be replaced with a beamsplitter.

Figure 2:
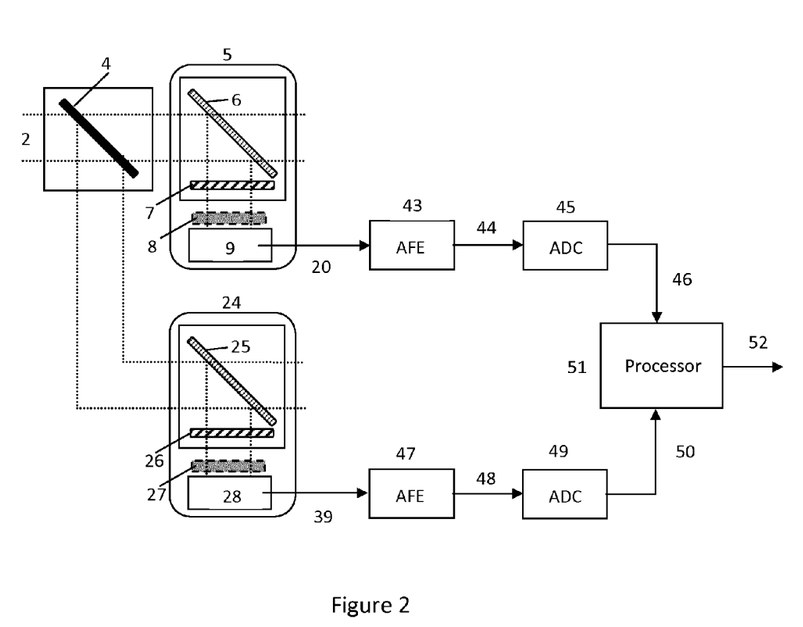
FIG. 2 illustrates how the wide dynamic range signal for the first luminescence colour, described in FIG. 1, is created. The outputs from the high gain semiconductor optical sensors for this luminescence colour are converted to analogue voltages and then digitized. These digital signals are transferred to a signal processing unit that contains a pre-determined algorithm which combines and weights these to produce an instantaneous wide dynamic range signal with high resolution, according to one embodiment of the invention.

FIG. 2 illustrates in more detail how the wide dynamic range signal for the first luminescence colour, described in FIG. 1, is created. The collected luminescence 2 is again transferred to a beamsplitter 4 that splits the light into 2 paths. Again for this first colour, the majority of light is detected using filter cell 5 which consists of a dichroic mirror 6 which reflects the wavelengths of interest and transmits the remaining spectrum to adjacent filter cells (not shown). The reflected light from the dichroic mirror 6 in this filter cell 5 is transferred to 1 or more high gain semiconductor optical sensors 9 via a bandpass filter 7 and an attenuating component 8. The remaining light from the beamsplitter 4 for the first colour of interest is detected by filter cell 24. Again, the light is reflected from the dichroic mirror 25 and transferred to 1 or more high gain semiconductor optical sensors 28 via a bandpass filter 26 and an attenuating component 27. Each of the outputs 20 and 39 from the sensor components 9 and 28 are connected to analogue front-end (AFE) components, 43 and 47, to convert the respective photocurrents 20 and 39 to analogue voltages 44 and 48 using transimpedance amplifiers or similar. These analogue signals are digitized using analogue to digital convertors (ADC) 45 and 49 and these digital signals 46 and 50 are transferred to a signal processing unit 51 that contains a pre-determined algorithm for this first colour. This algorithm combines and weights the digital outputs 46 and 49 for the spectral range of interest. This produces a pre-determined, instantaneous, wide dynamic range signal 52 for this colour of interest. The high gain settings of the sensors 9 and 28 maintain high resolution in the detection system over this dynamic range.

Figure 3:
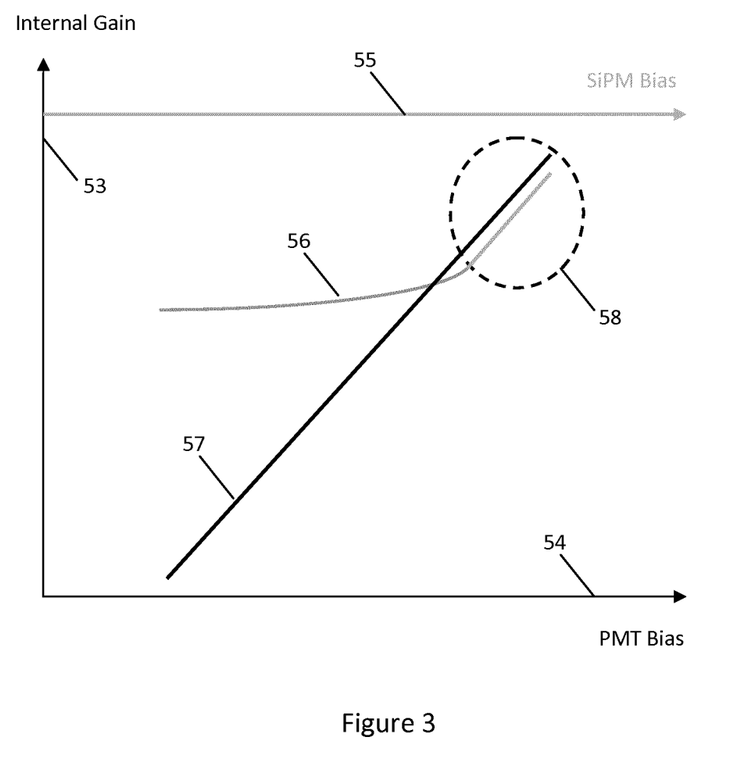
FIG. 3 illustrates the difference between the gain versus bias voltage profile of an industry standard high gain sensor photomultiplier tube (PMT) compared to the high gain semiconductor optical sensors used in the multi-colour detection described in this invention.

FIG. 3 illustrates the difference between the gain versus bias voltage profile of an industry standard high gain sensor photomultiplier tube (PMT) compared to a high gain semiconductor optical sensor. The PMT 57 produces a linearly increasing internal gain 53 profile with increasing PMT bias 54. The internal gain profile for high gain semiconductor optical sensors such as SiPMs 56 is non-linear and varies greatly with SiPM bias 55 as shown in FIG. 5. There is a limited region 58 for SiPMs where the gain profile is linear and of similar magnitude to PMTs. Therefore, to preserve high resolution in detection system using high gain semiconductor optical sensors, it is important to pre-tune the sensors' biases to be in this high gain region 58. As demonstrated in FIGS. 4 and 5, moving away from this high gain region 58 in this type of detection system can increase dynamic range but at the expense of resolution.

Figure 4:
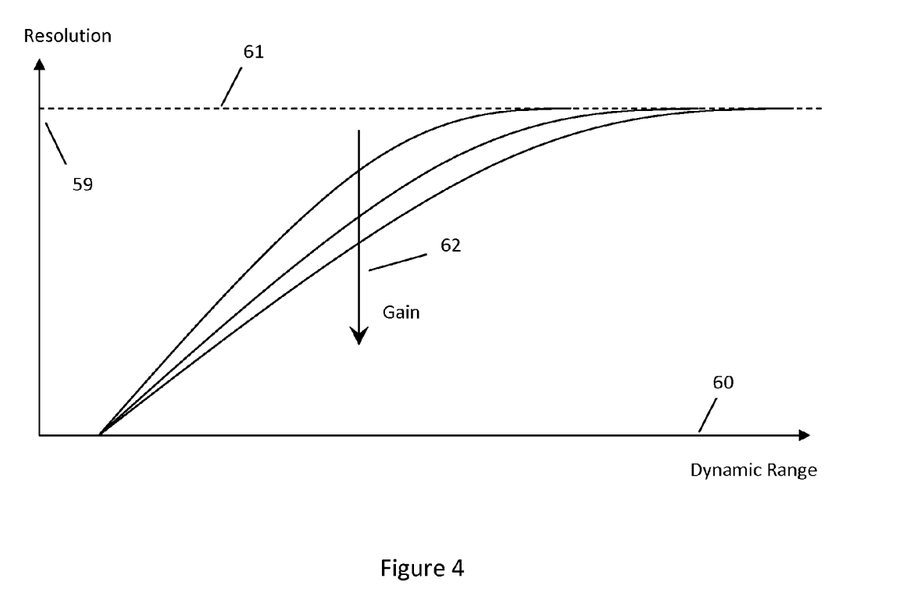
FIG. 4 illustrates the resolution limitations of high gain semiconductor optical sensors, according to the invention, when reducing their bias voltage or gain to detect bright optical signals.
Figure 5:
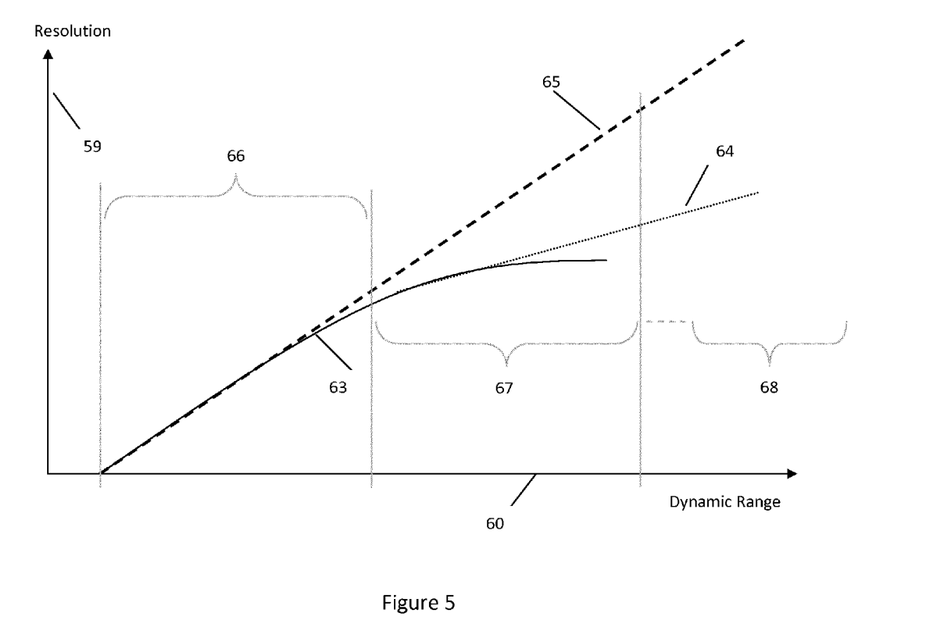
FIG. 5 illustrates the reconstruction of a wide dynamic range signal from multiple high gain semiconductor optical sensors using the method of changing the bias voltage to detect bright optical signals, the resolution limitations with this, or using beam splitting or light attenuation while maintaining the high internal gain in the sensors, to construct an ideal high resolution wide dynamic range signal.

FIG. 4 illustrates that a compromise between resolution and dynamic range is required for high gain semiconductor optical sensors, when varying their bias voltage or gain. This is of particular importance for solid-state sensors with internal gain such as SiPMs, where the gain is increased in the sensor by increasing its bias which enhances its ability to resolve between cellular samples of similar but different optical intensities.

It will be appreciated that high resolution in the detection system can be achieved by increasing the bias voltage to raise the detected luminescence from dimly stained samples above the noise floor of the system while also keeping a brighter sample of interest within the linear range of an individual sensor. To maximise the resolution in the sensor, requires increasing this bias to the point where the detected luminescence intensity between these two samples no longer increases, which is termed high resolution in this specification.

However, this increase in resolution 59 comes at the expense of dynamic range 60 for an individual high gain semiconductor optical sensor 9, as the sensor output would reach its saturation limit 61 at lower optical intensities. Resolution 59 here corresponds to the photocurrent output 20 of an optical sensor, its analogue voltage output 44 or its digitised equivalent 46. The saturation limit 61 corresponds to the optical sensor's photocurrent limit. As the gain of the sensor 9 or its bias voltage is reduced to detect brighter optical components and ensure it does not reach its saturation limit 61, the resolution 59 of the sensor decreases even though its dynamic range 60 increases. Therefore, reducing the bias voltage of the secondary sensor(s) to detect brighter optical powers from cellular or biological samples decreases the resolution of the sensor(s) despite expanding the dynamic range of the system. To counteract this resolution versus dynamic range compromise, the present invention uses optical power splitting to multiple sensors using beam splitters or uncoated mirrors to maintain the resolution of the sensors in high gain mode.

FIG. 5 also illustrates the resolution versus dynamic range compromise of the high gain semiconductor optical sensors. This figure shows the output response or resolution 59 from a single sensor 63 over the first optical range of interest 66. The output response from a secondary sensor 64 over the second optical range of interest 67 is also shown. The output response 64 generated in this case is done so by reducing the bias voltage or the gain of the sensor to look at this range 67 without saturating the sensor's output. The combination of these 63, 64 would produce a wide dynamic range detection system over these two optical ranges, 66, 67 and up to an $N^{th}$ optical range of interest 68 if N optical sensors were used. However, this system would be limited with regard to resolving between samples of interest with bright optical components. To overcome these resolution limitations, an ideal wide dynamic range detection system with additional high resolution is depicted by the system's output 65, where the light falling on the sensors in the optical ranges 67 up to 68 is attenuated using beamsplitter components or similar instead of reducing the sensors' gain. The system's output 65 per colour of interest is a combination of the sensor output 63 over the first optical range 66 and this is interleaved with the output from a secondary sensor which has the light levels falling on it attenuated, as described.

Defining wide dynamic range is achieved by using two or more sensors. The output 65 can produce a dynamic range dependent on the number of the sensors used in the detection system, while keeping the optimal resolving capability of the first sensor over the complete range. This compares to just three decades of dynamic range for any single sensor based system Any roll-off at the saturation limit of any of the single sensors 17 are pre-determined and eliminated by the pre-determined algorithm per colour in the processing unit.

Figure 6:
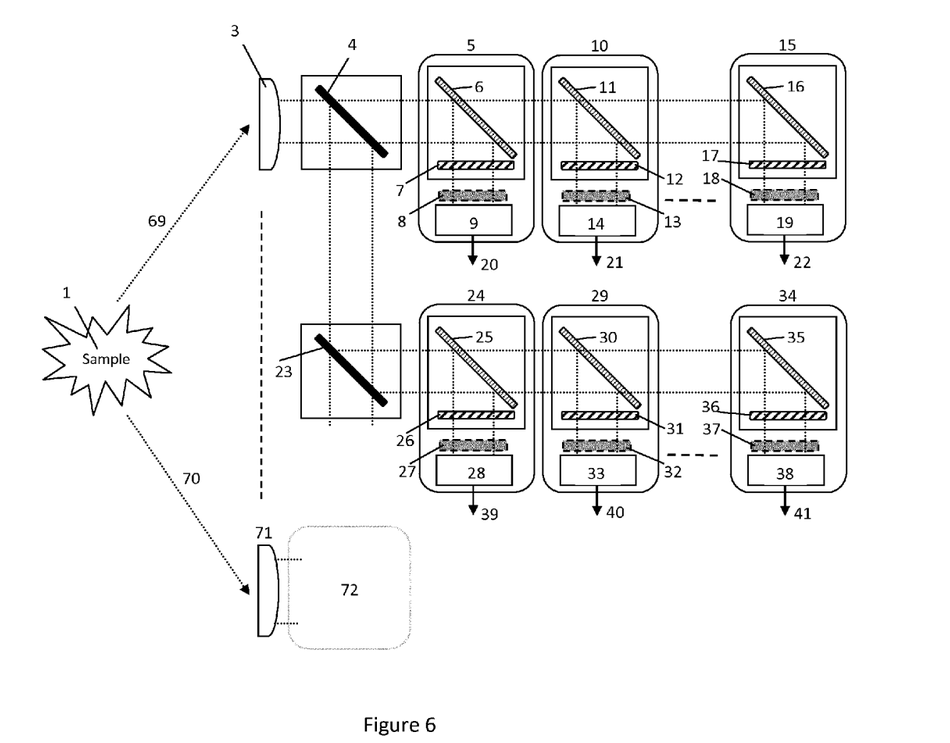
FIG. 6 illustrates another embodiment of the present invention using multiple collection points to transfer this luminescence to multiple high gain semiconductor optical sensors per colour. Again, splitting the light using a beamsplitter or similar over 1 or more sensors as described in the embodiment of FIG. 1 applies here. In this embodiment, the dynamic range can be extended further using multiple collection points as the method for generating a multi-colour high resolution, wide dynamic range detection system.

FIG. 6 illustrates another embodiment of the present invention using multiple collection points M to collect luminescence from N high gain semiconductor optical sensors per colour C. Again, splitting the light using a beamsplitter or similar over 1 or more sensors as described in FIG. 1 applies here as the method for generating a multi-colour high resolution, wide dynamic range detection system for use in microfluidic applications. Luminescence 69 and 70 emanating from a biological or cellular sample 1 is collected at 1 or M collection points using lens systems 3 to 71. For the luminescence 69 collected at 3, the pre-determined interleaved output for each colour is as described in the description of FIGS. 1 and 2. In this embodiment the dynamic range is extended further by collecting from M collection points with the dynamic range now determined by N sensors from these M collection points. The detection system described in FIGS. 1 and 2 can also be represent the detection system 72 connected to the lens system 71 for the $M^{th}$ collection point. In FIG. 5 the dynamic range 60 was determined by 1 or more high gain semiconductor optical sensors from 1 collection point, where in relation to FIG. 6 the dynamic range 60 represents N sensors from M collection points for each luminescence colour C where required. For each colour C, the outputs of these N sensors are similarly interleaved as described for FIG. 2 with a resulting extended dynamic range.

Figure 7:
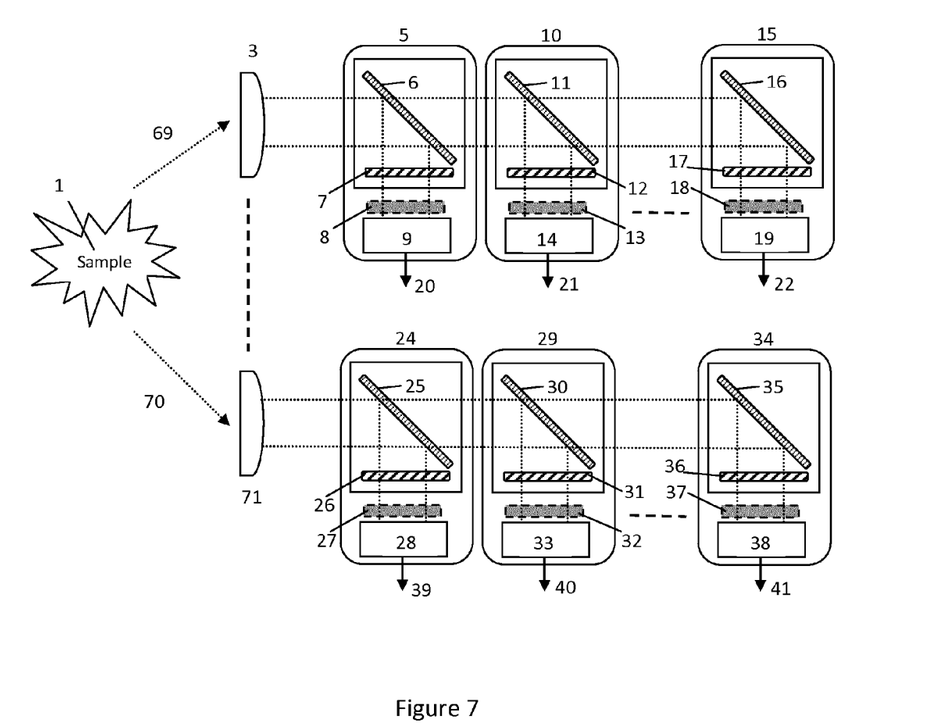
FIG. 7 illustrates an embodiment of the present invention using multiple light collection points instead of a beam splitting method for generating a high resolution, wide dynamic range detection system. Attenuating components are used on some of the sensors to extend the dynamic range of the system, while maintaining high resolution throughout.

FIG. 7 illustrates an embodiment of the present invention using a plurality of light collection points instead of a beam splitting method for generating a high resolution, wide dynamic range detection system. Luminescence 69 to 70 emanating from a biological or cellular sample 1, is collected at 1 or M collection points. The light collected from the first collection point is done by a lens system 3 while the lens system 71 collects the light from the $M^{th}$ collection point. At each of these collection points, the collected luminescence for each colour is transferred to 1 or more sensors. The primary collection lens system 3 transfers the luminescence to filter cells 5, 10 and 15 for the C colours of interest. For the first spectral region of interest, the light is detected using filter cell 5 which consists of a dichroic mirror 6 which reflects the wavelengths of interest and transmits the remaining spectrum to the adjacent filter cell 10. The reflected light from the dichroic mirror 6 is transferred to 1 or more high gain semiconductor optical sensors 9 via a bandpass filter 7 and an attenuating component 8, in embodiments where required. For the second spectral region of interest, the light is detected using filter cell 10 which consists of a dichroic mirror 11 which reflects the wavelengths of interest and transmits the remaining spectrum to the adjacent filter cell 15. The reflected light from the dichroic mirror 11 is transferred to 1 or more high gain semiconductor optical sensors 14 via a bandpass filter 12 and an attenuating component 13, in embodiments where required. For the $C^{th}$ spectral region of interest, the light is detected using filter cell 15 which consists of a reflective mirror 16 which reflects the remaining wavelengths of interest. The reflected light from the dichroic mirror 16 is transferred to 1 or more high gain semiconductor optical sensors 19 via a bandpass filter 17 and an attenuating component 18, in embodiments where required. Typically the sensors 19 in this first collection point do not use an attenuating component as these sensors will be used to detect any dim light components from the luminescence sample 1. For some embodiments this will not be the case. The attenuating components will therefore be typically used in the sensors connected to the remaining M collection points to provide a wide dynamic range while maintaining the sensors in their high internal gain region to sustain resolution for the C colours of interest. Therefore, for additional collection points such as the $M^{th}$ one lens system 71 transfers the luminescence from the sample 1 to filter cells 24, 29 and 34 for the same C colours of interest. For the first spectral region of interest of the $M^{th}$ collection point, the light is detected using filter cell 24 which consists of a dichroic mirror 25 which reflects the wavelengths of interest and transmits the remaining spectrum to the adjacent filter cell 29. The reflected light from the dichroic mirror 25 is transferred to 1 or more high gain semiconductor optical sensors 28 via a bandpass filter 26 and an attenuating component 27 where required. For the second spectral region of interest in the $M^{th}$ collection point, the light is detected using filter cell 29 which consists of a dichroic mirror 30 which reflects the wavelengths of interest and transmits the remaining spectrum to the adjacent filter cell 34. The reflected light from the dichroic mirror 30 is transferred to 1 or more high gain semiconductor optical sensors 33 via a bandpass filter 31 and an attenuating component 32, in embodiments where required. For the $C^{th}$ spectral region of interest for the lens system 71, the light is detected using filter cell 34 which consists of a reflective mirror 35 which reflects the remaining wavelengths of interest. The reflected light from the dichroic mirror 35 is transferred to 1 or more high gain semiconductor optical sensors 38 via a bandpass filter 36 and an attenuating component 37, in embodiments where required.

For each colour component, the photocurrent outputs 20 to 39, 21 to 40 and 22 to 41 from these N sensors are digitized as shown in the FIG. 2 description and interleaved using pre-determined algorithms, to create high resolution, wide dynamic range signals.

Figure 8:
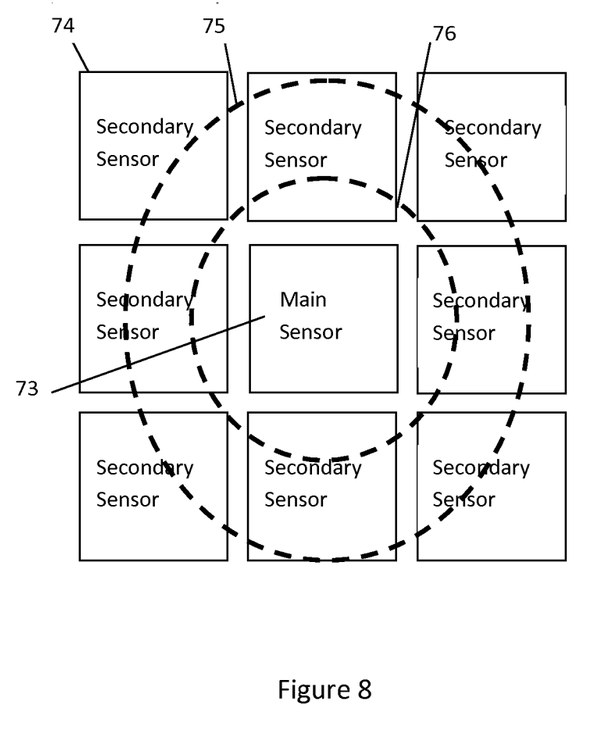
FIG. 8 illustrates another embodiment of the present invention using an array of high gain semiconductor optical sensors for each spectral range of interest at any collection point as a method for generating a multi-colour high resolution, wide dynamic range detection system. The area of the sensor array illuminated by the collected light beam can be varied and will determine the dynamic range of a given sensor array when the outputs of these are combined in a pre-determined algorithm per colour.

FIG. 8 illustrates another embodiment of the present invention using an array of high gain semiconductor optical sensors for each spectral range of interest at any collection point as a method for generating a multi-colour high resolution, wide dynamic range detection system. Luminescence 69 to 70 emanating from a biological or cellular sample 1 is collected at 1 or M collection points, and focused on an array of main 73, and secondary 74, high gain semiconductor optical sensors. The main sensor, 73, is positioned and configured so that it receives the maximum amount of collected luminescence. The secondary sensors, 74, are positioned such that they receive light not collected by the main sensor, 73. The main sensor, 73, should have the highest photon collection performance and will be used to measure dim levels of luminescence. The secondary sensors shall be designed to be the main measurement system for the brighter levels of luminescence. The luminescence collected shall be distributed over the sensor array. The area illuminated by the collected luminescence is indicated by the dotted regions 75 and 76. The array may be configured such that the main sensor receives all or most of the collected luminescence as indicated by region 76. It may also be configured such that a greater portion of the luminescence is distributed over the secondary sensors, 74 using the illumination region 75. The beam size will ultimately determine the dynamic range associated with each sensor array per colour when the outputs combined and weighted using pre-determined algorithms as discussed in other embodiments. The illumination region should ideally match the shape of the sensor array to optimize the amount of light collected; however in this embodiment a Gaussian beam is used for illustration purposes. An attenuating component, such as a lens system in this case, as used in the filter cells of FIG. 1-2, 6-7 adjusts the illumination spot sizes 75 and 76.

To achieve such spot size adjustment, the lens system can be moved relative to sensor array or otherwise the array is moved relative to the lens system.

It will be appreciated that the invention can be incorporated into multiple microfluidic analytical instruments including portable point of care analysers. This invention enables the various embodiments of such instruments presented herein. Such instruments include, for example, and without limitation, immunoassay analysers, clinical haematology analysers, flow and scanning cytometers, fluorimeters, and chemistry analysers. The specific biological targets can be in a microfluidic platform, where luminescence detection at different wavelengths over a wide optical range while maintaining high resolution can be achieved with the present invention.

The invention is not limited to the embodiments hereinbefore described but may be varied in both construction and detail.

The invention claimed is:

1. A multi-colour luminescence detection system in a microfluidic system, said detection system comprising:
    a first high gain semiconductor optical sensor, for each luminescence colour component from a cellular or biological sample in the microfluidic system, adapted to be biased at an optimal operating voltage or gain for detecting low light levels of luminescence emitted from the cellular or biological sample with high resolution;
    a second, optimally biased, high gain semiconductor optical sensor for each colour component adapted to detect light levels of luminescence higher than the levels of luminescence detected by the first high gain semiconductor optical sensor emitted from the cellular or biological sample with high resolution;
    a splitter for splitting light into at least a first light path and a second light path for each detected colour of luminescence, the first light path coupling the light to the first high gain semiconductor optical sensor and the second light path coupling the light to the second high gain semiconductor optical sensor, wherein the split ratio of the splitter is adapted to attenuate the light in the second light path; and
    a processor for processing per luminescence colour by combining and weighting the outputs from the first and second high gain semiconductor optical sensors using a signal processing unit, and providing an instantaneous multi-colour high resolution detection system over an extended dynamic range; wherein the first and second high gain semiconductor optical sensors comprise a SiPM sensor.

2. A detection system as in claim 1 comprising means for splitting the collected luminescence into specific wavelengths of interest using a coated beamsplitters/dichroic mirror and at least one optical filter.

3. A detection system as claimed in claim 1 wherein the splitter comprises a beam splitter.

4. A detection system as claimed in claim 1 wherein more than one optical detection point is used to collect the light from the emitted sample to generate an instantaneous high resolution signal over a wide dynamic range per colour.

5. A detection system as claimed in claim 1 wherein light emitted from the sample is coupled to a collector and passed through at least one optical component to attenuate the light level and delivered to said second optical sensor.

6. A detection system as claimed in claim 1 comprising a collector adapted to collect light from the sample and directed to a beam splitter before being passed to each filter cell.

7. A detection system as claimed in claim 1 comprising a collector adapted to collect light from the sample and directed to a beam splitter before being passed to each filter cell wherein the collector comprises a lens system.

8. A detection system as claimed in claim 3 wherein the beam splitter is adapted with two or more output ports for delivering light to each filter cell per colour.

9. A detection system as claimed in claim 3 wherein the beam splitter comprises an uncoated mirror, said mirror adapted to deliver maximum amount of light via a first port to the first high gain semiconductor optical sensor detecting low-end light levels while bright light components of the sample are detected simultaneously using the remaining light at the second port by said second sensor.

10. A detection system as claimed in claim 3 wherein the amount of light delivered from said first and second ports is dependent on the transmission or reflectance of the uncoated beam splitter.

11. A method of multi-colour luminescence detection in a microfluidic system, said method comprising the steps of:
    biasing a first high gain semiconductor optical sensor, for each luminescence colour component from a cellular or biological sample in the microfluidic system, at an optimal operating voltage or gain for detecting low light levels of luminescence emitted from the cellular or biological sample with high resolution;
    biasing a second, optimally biased, high gain semiconductor optical sensor for each colour component adapted to detect light levels of luminescence higher than the levels of luminescence detected by the first high gain semiconductor optical sensor emitted from the cellular or biological sample with high resolution
    splitting light into at least a first light path and a second light path for each detected colour of luminescence, the first light path coupling the light to the first high gain semiconductor optical sensor and the second light path coupling the light to the second high gain semiconductor optical sensor, wherein the split ratio is adapted to attenuate the light in the second light path; and
    processing per luminescence colour by combining and weighting the outputs from the first and second high gain semiconductor optical sensors using a signal processing unit, and providing an instantaneous multi-colour high resolution detection system over an extended dynamic range; wherein the first and second high gain semiconductor optical sensors comprise a SiPM sensor.

* * * * *